(12) United States Patent
Wozencroft

(10) Patent No.: US 11,317,928 B2
(45) Date of Patent: May 3, 2022

(54) SURGICAL GUIDE FOR POSITIONING A RESURFACING HEAD IMPLANT

(71) Applicant: Embody Orthopaedic Limited, London (GB)

(72) Inventor: Robert Michael Wozencroft, Central London (GB)

(73) Assignee: Embody Orthopaedic Limited, London (GB)

( * ) Notice: Subject to any disclaimer, the term of this patent is extended or adjusted under 35 U.S.C. 154(b) by 100 days.

(21) Appl. No.: 16/321,825

(22) PCT Filed: Jul. 31, 2017

(86) PCT No.: PCT/GB2017/052226
§ 371 (c)(1),
(2) Date: Jan. 29, 2019

(87) PCT Pub. No.: WO2018/025021
PCT Pub. Date: Feb. 8, 2018

(65) Prior Publication Data
US 2019/0167280 A1 Jun. 6, 2019

(30) Foreign Application Priority Data

Jul. 30, 2016 (GB) ...................... 1613199

(51) Int. Cl.
*A61B 17/17* (2006.01)
*A61B 17/16* (2006.01)
(Continued)

(52) U.S. Cl.
CPC ........ *A61B 17/175* (2013.01); *A61B 17/1668* (2013.01); *A61B 17/1721* (2013.01);
(Continued)

(58) Field of Classification Search
CPC ............ A61B 17/1637; A61B 17/1668; A61B 17/175; A61B 17/1721; A61B 2017/1602; A61B 2017/568; A61B 2017/00429
See application file for complete search history.

(56) References Cited

U.S. PATENT DOCUMENTS 8,236,001 B2 * 8/2012 Willi .................... A61B 17/175
606/89
8,696,717 B2 * 4/2014 Rock .................. A61B 17/7037
606/308
(Continued)

FOREIGN PATENT DOCUMENTS

CN 2519658 Y 11/2002
CN 110139613 A 8/2019
(Continued)

OTHER PUBLICATIONS

"European Application Serial No. 17748902.8, Resposne filed Sep. 13, 2019 to Office Action dated Mar. 19, 2019", 17 pgs.
(Continued)

*Primary Examiner* — Anu Ramana
(74) *Attorney, Agent, or Firm* — Schwegman Lundberg & Woessner, P.A.

(57) ABSTRACT

The present invention relates to a guide for positioning a resurfacing head implant into the appropriate position and angles on the femur bone. The present invention therefore provides a guide system for an implantable device (e.g. a resurfacing head implant), said guide system comprising a first component arranged to act as a clamp and a second component arranged to interact with the first component to prevent movement of said first component when clamped.

17 Claims, 14 Drawing Sheets

(51) Int. Cl.
*A61B 17/00* (2006.01)
*A61B 17/56* (2006.01)

(52) U.S. Cl.
CPC ... *A61B 17/1637* (2013.01); *A61B 2017/0023* (2013.01); *A61B 2017/00429* (2013.01); *A61B 2017/1602* (2013.01); *A61B 2017/568* (2013.01)

(56) References Cited

U.S. PATENT DOCUMENTS

| | | | | |
|---|---|---|---|---|
| 8,715,289 | B2* | 5/2014 | Smith | A61B 17/56 606/87 |
| 8,858,561 | B2* | 10/2014 | White | A61B 17/175 606/86 R |
| 9,572,590 | B2* | 2/2017 | Singhal | A61B 17/175 |
| 9,629,642 | B2* | 4/2017 | Johannaber | A61B 17/17 |
| 2005/0113841 | A1 | 5/2005 | Sheldon et al. | |
| 2009/0254093 | A1 | 10/2009 | White et al. | |
| 2010/0114180 | A1 | 5/2010 | Rock et al. | |
| 2016/0081758 | A1 | 3/2016 | Bonutti | |

FOREIGN PATENT DOCUMENTS

| | | |
|---|---|---|
| EP | 1588669 A1 | 10/2005 |
| EP | 2193752 A1 | 6/2010 |
| JP | H05270188 A | 10/1993 |
| WO | WO-03055400 A1 | 7/2003 |
| WO | WO-2009001109 A1 | 12/2008 |
| WO | WO-2012021849 A2 | 2/2012 |
| WO | WO-2018025021 A1 | 2/2018 |

OTHER PUBLICATIONS

"International Application Serial No. PCT/GB2017/052226, International Search Report dated Dec. 12, 2017", 7 pgs.

"International Application Serial No. PCT/GB2017/052226, Invitation to Pay Additional Fees dated Oct. 18, 2017", 12 pgs.

"International Application Serial No. PCT/GB2017/052226, Written Opinion dated Dec. 12, 2017", 8 pgs.

"Chinese Application Serial No. 201780047375.5, Office Action dated Jul. 5, 2021", w/ English Translation, 18 pgs.

"Chinese Application Serial No. 201780047375.5, Response filed Oct. 29, 2021 to Office Action dated Jul. 5, 2021", w/ English claims, 18 pgs.

"Chinese Application Serial No. 201780047375.5, Office Action dated Jan. 4, 2022", with English translation, 9 pages.

"Chinese Application Serial No. 201780047375.5, Response filed Feb. 7, 2022 to Office Action dated Jan. 4, 2022", with English claims, 14 pages.

* cited by examiner

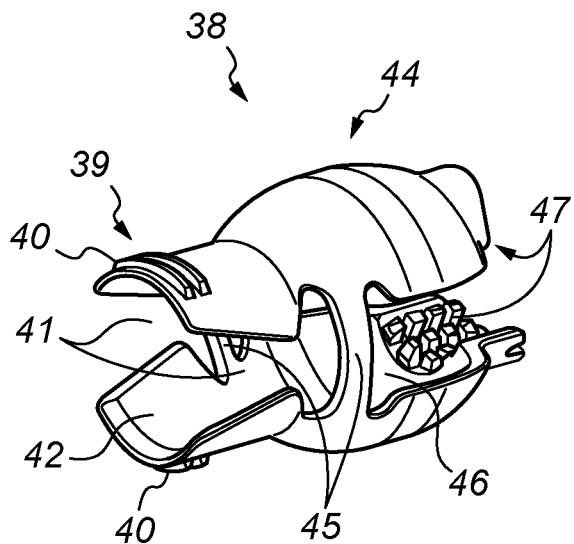
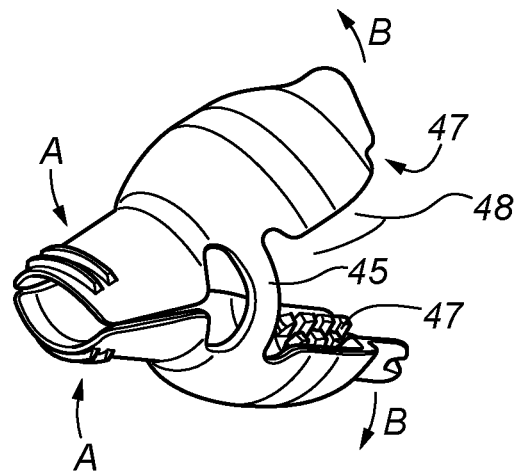
Figure 20
Figure 21
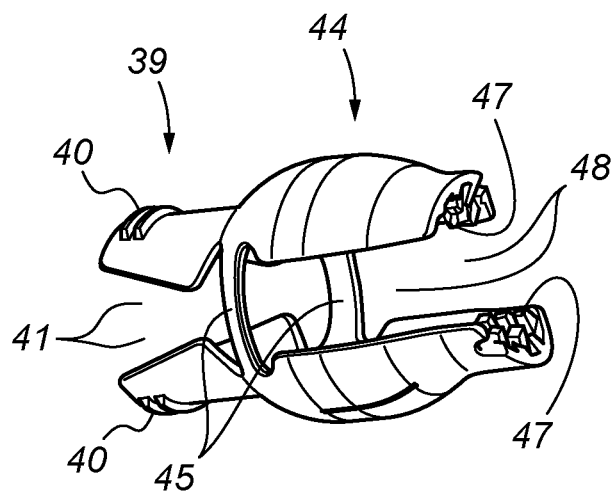
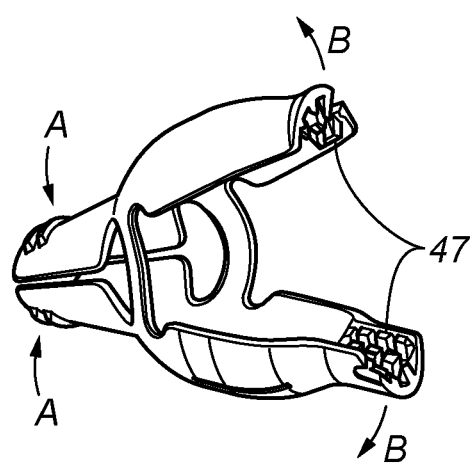
Figure 22
Figure 23

SURGICAL GUIDE FOR POSITIONING A RESURFACING HEAD IMPLANT

This application is a U.S. National Stage Application under 35 U.S.C. 371 from International Application Serial No. PCT/GB2017/052226, filed on Jul. 31, 2017, and published as WO 2018/025021 A1 on Feb. 8, 2018, which claims priority to United. Kingdom Application No. 1613199.7, filed on Jul. 30, 2016, the benefit of priority of each of which is claimed hereby, and each of which are incorporated by reference herein in its entirety.

During a hip resurfacing operation the head of the femur is retained and capped with a head implant with a spherical bearing of a similar size to the natural joint. The bone socket in the pelvis is reamed to approximately a hemispherical shape and a thin walled cup implant is fitted to completely reline the joint with an artificial bearing. In order to regain natural range of motion and to ensure the bearing functions well over a long period of time, it is very important to position both the head and cup implants correctly relative to the natural bone and soft tissue structures. This is particularly challenging in the diseased hip where the head of the femur is often misshapen and the acetabular socket has migrated slightly out of position. This can be misleading when it comes to positioning the implant components. Furthermore, the surgeon has limited access and visibility during the operation, so it can be difficult to visualise landmarks and to judge the orientation of the bones.

When the surgeon positions a resurfacing head implant on the femur bone the following factors are considered:
1. Femoral head/neck size: The choice of head implant size should be approximately the same as the natural head size, at the same time there must be enough bone available on the head to support the implant fully and it is vital that the cutters used to prepare the head do not encroach into the femoral neck (known as notching) as it weakens the bone and can cause femoral neck fracture postoperatively.
2. Varus/valgus angle: This is the angle between the femur shaft axis and the head implant axis and should be in the range 135-145 degrees so that the load is transferred through the implant without putting undue stress on the bone.
3. Version angle: This is the forward tilt angle of the femoral neck relative to the frontal anatomical plane. It is unique for each patient and usually within the range 15-25 degrees. The surgeon will try to place the head axis according to the natural femoral neck version angle for a specific patient.

Patient specific guides are sometimes used in joint replacement operations to help position implants. They are defined and constructed preoperatively based on three-dimensional digital images of the patient's joints. The digital images of the patient's joint can be reconstructed from medical scans of the patient using commercially available CAD (Computer Aided Design) and/or other specific planning software. The surgeon or skilled technician interacts with the software to place the implant in the desired positions relative to the patient's scanned bones. A patient matched guide is then defined and constructed using rapid prototyping techniques such as additive manufacture. These guides are devised to fit exactly with a patients exposed bone surfaces intraoperatively so that the implants can be directed exactly to their planned positions. The advantage of a patient specific head guide for the resurfacing head is that multifactorial variables listed (1-3) above are all resolved simultaneously according to a pre-operative plan as the guide fits exactly into a distinct position on the femur bone.

The present invention is a guide for positioning a resurfacing head implant into the appropriate position and angles on the femur bone.

The present invention therefore provides a guide system for an implantable device (e.g. a resurfacing head implant), said guide system comprising a first component arranged to act as a clamp and a second component arranged to interact with the first component to prevent movement of said first component when clamped The invention also provides a guide system for an implantable device, said guide system comprising a first component arranged to act as a clamp, said first component comprising at least one actuating portion and at least one jaw portion, said actuating and jaw portions arranged either side of at least one hinge region, said actuating portion being positioned at a proximal region of the first component and a distal jaw portion being positioned at a distal region of the first component, wherein said distal region further comprises a locking mechanism to restrict or prevent opening of the distal jaw portion when said locking mechanism is activated.

The guide system generally comprises a proximal region, said proximal region comprising an actuating portion and proximal jaw portion formed by the walls of said first component. The proximal region preferably further comprises a cavity defined by the walls of said first component between the actuating portion and proximal jaw portion. This cavity permits access to a distal region of the first component, for example along a longitudinal axis of the guide system.

The first component preferably comprises at least one actuating portion and at least one jaw portion. In some preferred arrangements, the at least one actuating portion and at least one jaw portion each comprises opposing arms arranged either side of a hinge region In some aspects, the actuating portion and distal jaw portion are arranged on either side of the hinge region such that when the actuating portion is compressed the jaw portion expands, and when the actuating portion is relaxed the jaw portion closes. In preferred arrangements, the hinge region lies substantially perpendicular to the longitudinal axis of the first component. In order to effect suitable pivoting, the hinge region is typically offset from the longitudinal axis of the guide system.

In preferred arrangements, the hinge region can be formed from the same material as the first component and preferably is integral with the first component, the first component and the hinge region thereby forming a single piece.

Alternatively, the hinge region can be articulated, with the first component comprising more than one piece which are connected via the hinge region.

The actuating portion can comprise at least two opposing arms. In certain aspects of the invention, the arms of the actuating portion are substantially the same length. This is useful when there is a second component involved and where that second component is fixed to the actuating portion.

The arms of the actuating portion preferably extend (away) from the proximal portion of the first component, preferably extending substantially perpendicular to the longitudinal axis of the first component. This arrangement can provide a suitable lever around the hinge acting as a pivot whereby relatively small movements of the actuating portion can result in larger movements of the jaw portion in order to manipulate the jaw portion around the bone.

The first component of the guide system will preferably comprise a distal jaw portion being positioned at a distal region of the first component. This is the region that will typically be placed around the femur neck when the guide is in position. In preferred arrangements, the distal region further comprises a locking mechanism to restrict or prevent opening of the distal jaw portion when the locking mechanism is activated. This provides for a more secure guide, which is relatively immobile when locked in position. It has been found that a suitable locking mechanism comprises a latch. However, the skilled person will be aware of other arrangements of locking mechanism that can be associated with the guide system (e.g. not necessarily at the distal jaw portion) which can afford a suitable locking action to the distal jaw portion.

The locking mechanism (e.g. a latch) can be configured either:
(i) to have one locking position (e.g. in a patient specific guide, where the bone has been accurately profiled prior to surgery and the guide system has been manufactured specifically to conform to the profile); or
(ii) to have a plurality of locking positions which allow a stepped progression of tightening the distal jaw portion (e.g. in a generic guide, where the patient's bone has not been profiled pre-operatively and where, therefore, the surgeon must work with the expected variation in bone sizes that will occur across a range of patients).

This facility to adjust the locking mechanism provides suitable leeway to provide a firm and stable securement of the guide system to the bone, irrespective of the actual shape and size of the bone.

Preferably the latch is releasable, so that after the surgery or in cases where the guide system needs to be readjusted during surgery the distal jaw portion can be released from its grip around the femur head and readjusted or removed, as necessary.

In the invention, the guide system can be made for a specific patient by using preoperative scans on the bones that will undergo the surgery. In such cases, the jaw portion of the guide (e.g. the distal jaw portion) can be profiled to closely match the patient's bone structure. In this regard, the jaw portion may have a gripping portion which is profiled to precisely align with the patient's femoral neck or other bone of interest such that a secure connection is made during clamping of the guide to the bone.

In other cases, a generic profile can be manufactured which will nevertheless still fit relatively snuggly according to the selection of an approximately sized guide in respect of the size of the bone/patient. In such scenarios, the use of a locking mechanism and a second component which interacts with the first component in order to securely clamp the first component to the bone may be quite important.

In embodiments where the guide is used for operating on the femur, it will be appreciated that the femur has a neck which is not symmetrical. Typically, the inferior (underside) portion of the neck presents a longer region of bone than does the superior (upper side). Therefore, although the arms of the jaw portion can be substantially the same length, in some embodiments the arms of the jaw portion are not the same length. In these cases, the arms of the jaw portion that are intended to contact the inferior region of the neck can be longer than the opposing arms of the jaw portion. Such an asymmetry in the jaw portion can lead to a greater stability and clamping force of the guide on the femur neck.

As well as differing lengths, the profile of the arms of the jaw portion may also be asymmetrically arranged as looked at in a plan view. This is because the neck of the femur is not a perfect cylinder but tends to be shaped asymmetrically. In some guides, the gripping portions on the jaws may therefore also be asymmetrically profiled in order to more closely fit the profile of the neck of the femur.

Furthermore, the distal jaw portion can comprise at least one gripping portion, wherein the gripping portion is profiled to increase frictional force with the intended item to be gripped. Such a gripping portion may for example comprise a plurality of flexible fingers.

As discussed in more detail below, the actuating portion and jaw portion typically are arranged on either side of a hinge region such that when the actuating portion is compressed the jaw portion expands, and when the actuating portion is relaxed the jaw portion closes.

In the preferred use of the device, the first component must fit over a femur head. This is partly achieved by expanding the jaw portion such that the arms of the jaw portion can fit over the femur head and then be released onto the femur neck in a clamping/gripping manner. However, it will be appreciated that the femur head is a ball joint, and thus presents a large body now confined within the guide. To this end, the guide is designed to define a cavity in the first component to accommodate the femur head. Such a cavity is typically defined by the walls of the actuating portion and jaw portions. Preferably the cavity lies between the actuating portion and the jaw portion. The cavity generally has a larger profile than the rest of the first component, which reflects the ball-like structure of the femur head. In some cases the cavity is a ballooned (expanded) profile, and in some circumstances this can be reasonably/approximately spherical.

Since the primary purpose of the guide is to build a solid framework for performing drilling and shaping of the femur head, it is preferred that such drilling and shaping is carried out when the guide is in a clamped arrangement around the bone. In this regard, therefore, the proximal portion of the guide system is arranged such that access to the cavity is permitted. As the femur head lies within the cavity, access to the femur head is thereby permitted for drilling and/or shaping activities.

In order to present a secure clamping arrangement, in preferred scenarios of the guide system there is a second component present and wherein the second component assists in preventing the first component from unclamping. Generally this is achieved by the second component interacting with the proximal region of the first component.

Generally this interacting is achieved by the proximal region of the first component and second component having complementary means for attaching to each other, such as a screw thread or a bayonet fitting. Preferably the second component comprises a bayonet fitting or press fit which is complementary to fixings on the proximal region of the first component to allow the second component to be securely fitted to the first component.

Preferably the second component is arranged such that it interacts with both sides of the proximal region of the first component in order to prevent the proximal region of the first component from expansion or compression.

Since drilling activities are important in order to position a guide rod for subsequent reaming of the bone surface, and thereafter implantation of the ball replacement, the guide system can further comprise a third component, said third component arranged to act as a guide for a drill bit.

The third component may be integrated with said second component, such that the second component also comprises as part of it the third component.

Alternatively, the third component is removably attachable to said second component. For example via e.g. complementary screw and thread arrangements on the second and third components, or e.g. complementary bayonet fittings on said second and third components.

The third component will typically have a shaft through which subsequent drill guides/drill bits can pass in order for accurate drilling on the surface of the femur head. In this regard, it is often important that there should be no movement of the shaft during drilling operations. In some embodiments, the third component may therefore be designed to interact with the second component in a manner which prevents any undesired movement of the drill shaft. In certain arrangements, the third component comprises support fins. These support fins can be arranged to contact an inner longitudinal surface of said second component. Using fins can save on material during the manufacturing process whilst still providing required support/strength, which saves time and money.

The guide system of the present invention can also further comprises a drill guide. Optionally, said drill guide is associated with said third component in order to correctly align a drill bit through the guide.

The guide system may also comprise a guide rod which is placed into the hole drilled by a drill bit and which is used to guide a reamer onto the surface of the femur head in order to achieve accurate shaping of the head.

To this end, the guide system of the invention may also further comprise a rotary cutter.

The guide system may also be used in a method of resurfacing a femoral head, said method comprising placing a guide over a femoral head, said guide comprising a first component arranged to act as a clamp, said first component comprising an actuating portion in a proximal region of the first component and at least one jaw portion, said at least one jaw portion comprising a proximal jaw portion in said proximal region of said first component, said actuating and jaw portions arranged either side of a hinge region, wherein said proximal region further comprising a cavity defined by the walls of said first component between the actuating portion and proximal jaw portion and wherein the cavity permits access to a distal region of the first component.

Preferably the first component is positioned by squeezing the actuating portion resulting in an expansion of the distal jaw portion in a distal region of said first component, the jaw portion is thereafter placed over the femoral head, and thereafter the actuating portion is released such that the jaw portion relaxes around the femoral neck.

The femoral head sits within the cavity defined by the walls of the proximal region of the first component and/or distal jaw portions.

The distal jaw portion can then be locked in position by the locking mechanism.

The method further comprises connecting a second component to said proximal portion of said first component, said second component thereby restricting the first component from further movement. Optionally, a third component is attached to said second component, said third component comprising a guide for a drill bit.

Thereafter, a drill guide is placed in the third component and a drill bit is placed through the guide and wherein the femoral head is drilled. Having drilled a hole, a guide rod is place in the drilled hole in the head of the femur, the third component is removed and a rotary cutter is placed over the guide rod and through the second component in order to cut the head of the femur.

After appropriate cutting, the remaining components are removed.

There is also provided a guide which positions a drilled hole in the femur to define the central axis of the resurfacing head implant in accordance with a preoperative plan or in accordance with the generic shape of a femoral neck.

Furthermore, the depth of a planar face cut on the femoral head is controlled by a feature of the guide in accordance with a preoperative plan, and/or in relation to the top of the femoral head.

The first component may be made from a plastics material (e.g. nylon). Such a material is advantageous as it provides the hinge region with some resilience such that it flexes between an activated (on manipulation) and a relaxed state. In certain embodiments the first component is made from additive manufacturing (for example selective laser sintering (SLS)). Likewise the second and/or third components can also be made from the same material and in the same manner as the first component.

The invention also provides for a computer-readable medium having computer-executable instructions adapted to cause a 3D printer to print a first component and/or second component and/or a third component of a guide system as defined herein.

The present invention also provides a guide system for an implantable device, said guide system comprising a first component arranged to act as a clamp, said component comprising an actuating portion and a jaw portion, said actuating and jaw portions arranged either side of a hinge region, wherein there is a cavity in the component defined by the walls of said component between the actuating portion and jaw portion and wherein the actuating portion is arranged such that access to the cavity is permitted via the actuating portion.

In certain arrangements, there can be provided at least one locking means in the region of the jaw portion. This locking mechanism can act to restrict or prevent opening of the distal jaw portion when said locking mechanism is activated. This can help to secure the jaw portion around the femur head when the guide is in use. Typically, the locking mechanism will be positioned to the side of the jaw portion so as not to compromise access to the cavity of the jaw portion from the distal end. In some forms, the locking means can comprise a latch. Such a latch may have a ratchet feature, where there are a number of positions to which the latch can be tightened. Other suitable mechanisms will be well known to the skilled person. In some arrangements there may be a locking mechanism on either side of the jaw portion, to effect even more securing over the femur neck when the guide is in use. It is preferred that there should be relatively easy access to the one or more locking mechanisms when the guide is in place, so that the user can activate the locking mechanism and also release it in order to be able to remove the guide once it has been appropriately used. Easier access may be provided via the use of longer tabs or the like on the locking mechanism(s) which can be used to activate and release the mechanisms from a distance if the actual locking mechanism itself is hard to access when in use due to the proximity of e.g. soft tissue or bone.

The locking mechanism (e.g. a latch) can be configured either:

(i) to have one locking position (e.g. in a patient specific guide, where the bone has been accurately profiled prior to surgery and the guide system has been manufactured specifically to conform to the profile); or (ii) to have a plurality of locking positions which allow a stepped progression of tightening the distal jaw portion (e.g.

in a generic guide, where the patient's bone has not been profiled pre-operatively and where, therefore, the surgeon must work with the expected variation in bone sizes that will occur across a range of patients).

This facility to adjust the locking mechanism provides a suitable leeway to provide a firm and stable securement of the guide system to the bone, irrespective of the actual shape and size of the bone.

The first component generally comprises an actuating portion and a jaw portion. The actuating portion and jaw portion each comprises opposing arms arranged around a hinge, in a similar arrangement as a clothes peg.

The actuating portion and the jaw portion preferably each comprises at least two opposing arms, optionally 2, 3, 4, 5 or 6 opposing arms. The number of arms on the actuating portion and the jaw portion does not necessarily need to be the same.

In certain aspects of the invention, the arms of the actuating portion are substantially the same length. This is useful when there is a second component involved and where that second component is fixed to the actuating portion.

The actuating portion will preferably provide a substantially cylindrical profile. It will be appreciated that the cylindrical profile does not need to be a fully formed cylinder. Instead, the walls of the actuating portion can have a number of gaps between the arms that make up the actuating portion. This is advantageous as it allows the compression and expansion of the opposing arms of the actuating portion in order to activate the jaw portion of the first component. By cylindrical it is meant that a substantially cylindrical profile is obtained if one were to imagine extension of the wall of the arms to a substantially cylindrical end point.

In the invention, the guide system can be made for a specific patient by using preoperative scans on the bones that will undergo the surgery. In such cases, the jaw portion of the guide can be profiled to closely match the patient's bone structure. In this regard, the jaw portion may have a gripping portion which is profiled to precisely align with the patient's femoral neck or other bone of interest such that a secure connection is made during clamping of the guide to the bone.

In other cases, a generic profile can be manufactured which will nevertheless still fit relatively snuggly according to the selection of an approximately sized guide in respect of the size of the bone/patient. In such scenarios, the use of a second component which interacts with the first component in order to securely clamp the first component to the bone may be quite important.

In embodiments where the guide is used for operating on the femur, it will be appreciated that the femur has a neck which is not symmetrical. Typically, the inferior (underside) portion of the neck presents a longer region of bone than does the superior (upper side). Therefore, although the arms of the jaw portion can be substantially the same length, in some preferred embodiments the arms of the jaw portion are not the same length. In these cases, the arms of the jaw portion that are intended to contact the inferior region of the neck can be longer than the opposing arms of the jaw portion. Such an asymmetry in the jaw portion can lead to a greater stability and clamping force of the guide on the femur neck.

As well as differing lengths, the arms of the jaw portion may also be asymmetrically arranged as looked at in a plan view. This is because the neck of the femur is not a perfect cylinder but tends to be shaped asymmetrically. In some guides, the gripping portions on the jaws may therefore also be asymmetrically profiled in order to more closely fit the profile of the neck of the femur.

As discussed in more detail below, the actuating portion and jaw portion typically are arranged on either side of a hinge region such that when the actuating portion is compressed the jaw portion expands, and when the actuating portion is relaxed the jaw portion closes.

In the preferred use of the device, the first component must fit over a femur head. This is partly achieved by expanding the jaw portion such that the arms of the jaw portion can fit over the femur head and then be released onto the femur neck in a clamping/gripping manner. However, it will be appreciated that the femur head is a ball joint, and thus presents a large body now confined within the guide. To this end, the guide is designed to define a cavity in the first component to accommodate the femur head. Such a cavity is typically defined by the walls of the actuating portion and jaw portions. Preferably the cavity lies between the actuating portion and the jaw portion, optionally in the region of the hinge. The cavity generally has a larger profile than the rest of the first component, which reflects the ball-like structure of the femur head. In some cases the cavity is a ballooned (expanded) profile, and in some circumstances this can be reasonably/approximately spherical.

Since the primary purpose of the guide is to build a solid framework for performing drilling and shaping of the femur head, it is preferred that such drilling and shaping is carried out when the guide is in a clamped arrangement around the bone. In this regard, therefore, the actuating portion is arranged such that access to the cavity is permitted via the actuating portion. As the femur head lies within the cavity, access to the femur head is thereby permitted for drilling and/or shaping activities.

In order to present a secure clamping arrangement, in preferred scenarios of the guide system there is a second component present and wherein the second component prevents the first component from unclamping. Generally this is achieved by the second component interacting with the actuating portion.

Generally this interacting is achieved by the actuating portion and second component having complementary means for attaching to each other, such as a screw thread or a bayonet fitting.

Preferably the second component is arranged such that it interacts with both sides of the actuating portion in order to prevent the actuating portion from expansion or compression.

Since drilling activities are important in order to position a guide rod for subsequent reaming of the bone surface, and thereafter implantation of the ball replacement, the guide system can further comprise a third component, said third component arranged to act as a guide for a drill bit.

The third component may be integrated with said second component, such that the second component also comprises as part of it the third component.

Alternatively, the third component is removably attachable to said second component. For example via e.g. complementary screw and thread arrangements on the second and third components, or e.g. complementary bayonet fittings on said second and third components.

The third component will typically have a shaft through which subsequent drill guides/drill bits can pass in order for accurate drilling on the surface of the femur head. In this regard, it is often important that there should be no movement of the shaft during drilling operations. In some embodiments, the third component may therefore be designed to interact with the second component in a manner which prevents any undesired movement of the drill shaft. In certain arrangements, the third component comprises support fins. These support fins can be arranged to contact an inner longitudinal surface of said second component. Using fins can save on material during the manufacturing process whilst still providing required support/strength, which saves time and money.

The guide system of the present invention can also further comprises a drill guide. Optionally, said drill guide is associated with said third component in order to correctly align a drill bit through the guide.

The guide system may also comprise a guide rod which is placed into the hole drilled by a drill bit and which is used to guide a reamer onto the surface of the femur head in order to achieve accurate shaping of the head.

To this end, the guide system of the invention may also further comprise a rotary cutter.

The guide system may also be used in a method of resurfacing a femoral head, said method comprising placing a guide over a femoral head, said guide comprising a component arranged to act as a clamp, said component comprising an actuating portion and a jaw portion, said actuating and jaw portions arranged either side of a hinge region, wherein there is a cavity in the first component defined by the walls of the actuating and jaw portions and wherein the actuating portion is arranged such that access to the cavity is permitted via the actuating portion.

Preferably the first component is positioned by squeezing the actuating portion resulting in an expansion of the jaw portion, the jaw portion is thereafter placed over the femoral head, and thereafter the actuating portion is released such that the jaw portion relaxes around the femoral neck.

The femoral head sits within the cavity defined by the walls of the actuating and jaw portions.

The method further comprises connecting a second component to said actuating portion of said first component, said second component thereby preventing the first component from further movement. Optionally, a third component is attached to said second component, said third component comprising a guide for a drill bit.

Thereafter, a drill guide is placed in the third component and a drill bit is placed through the guide and wherein the femoral head is drilled. Having drilled a hole, a guide rod is place in the drilled hole in the head of the femur, the third component is removed and a rotary cutter is placed over the guide rod and through the second component in order to cut the head of the femur.

After appropriate cutting, the remaining components are removed.

There is also provided a guide which positions a drilled hole in the femur to define the central axis of the resurfacing head implant in accordance with a preoperative plan or in accordance with the generic shape of a femoral neck.

Furthermore, the depth of a planar face cut on the femoral head is controlled by a feature of the guide in accordance with a preoperative plan, and/or in relation to the top of the femoral head.

The first component may be made from a plastics material (e.g. nylon). Such a material is advantageous as it provides the hinge region with some resilience such that it flexes between an activated (on manipulation) and a relaxed state. In certain embodiments the first component is made from additive manufacturing (for example selective laser sintering (SLS)). Likewise the second and/or third components can also be made from the same material and in the same manner as the first component.

The invention also provides for a computer-readable medium having computer-executable instructions adapted to cause a 3D printer to print a first component and/or second component and/or a third component of a guide system as defined herein.

The main body of the guide consists of two approximately cylindrical rings, one at each end, joined together by connecting struts. One ring is intended to be positioned around the femoral neck (neck ring) and the other is positioned at the opposite side of the femoral head (head ring). Both rings have an integral hinge on one side and an opening at the other side. The two hinges are arranged to be axially aligned, so that they act together (similar to two hinges on a gate or door). The head ring has two paddle features which extend outwards to the other side of the hinge. When the paddles are pressed together (for example between thumb and forefinger) the two halves of the main body, are hinged apart similar to a hair claw. This allows it to be assembled over the femoral head/neck bone, either from one end or from the side during the resurfacing operation. The neck ring has a latch at the opening side (opposite the hinge) for fastening it closed. Preferably the main body is manufactured in plastic in one piece with integral resilient hinges. However it could be manufacture in two or more parts with articulating hinges.

A separate collar (either one or two part) assembles over the head ring both to hold it in the closed position and to act as a guide for drilling. The collar also has a latch mechanism to hold it in the fully assembled position which can be manually released to remove it. With both the neck ring latch closed and the collar assembled over the head ring, the head guide becomes rigid which is important for the accuracy of the drilling function.

Preferably the main body and collar are manufactured in plastic (for example nylon) by an additive manufacturing process. The skilled person is aware of a number of different types of additive manufacturing processes, for example selective laser sintering (SLS) or stereolithography (SLA). Alternatively these parts could be moulded in plastic, for example by injection moulding or cold curing casting resin. Alternatively they could be manufactured in plastic by any other means, including machining.

Preferably a metal drill tube with a spiked end is inserted into the central hole of the collar. The spiked end slides down to contact the femoral head and the spikes embed into the bone slightly. Then a drill (for example 5 mm in diameter) is passed through the drill tube and a hole is drilled into the femur bone corresponding to the central longitudinal axis of the resurfacing head implant. The spiked end ensures that the drill enters the bone without deviating off line.

There are a number of variants of the head guide, each having in common the features described above. They are described below separated for ease of reading. However, features described in one arrangement can be used with features described in another embodiment.

Patient Specific Head Guide

In this variant the internal shape of the neck ring is defined preoperatively to exactly fit to the specific patient's femoral neck bone. The two halves of the neck ring hinge close around the femoral neck and a distinct position is found so that the guide is orientated according to a preoperative plan. The neck ring extends almost fully round the femoral neck so the ring will only close properly in the distinct position it is intended to fit. Once the neck ring latch is closed, it is very firm and stable on the femoral neck bone. Preferably the separate collar is in two parts (collar and collar insert) and the collar insert is fitted into the collar via a bayonet fitting.

Alternatively, a screw thread or friction fit could be used to attach the collar insert. The assembled collar is fitted onto the main body via a sliding fit and retained in position by a latch feature. Preferably a metal drill tube with a spiked end is inserted into the central hole of the collar insert and a drill (for example 5 mm in diameter) is then passed through the drill tube and a hole is drilled into the femur bone corresponding to the central longitudinal axis of the resurfacing head implant. The drill tube and insert are removed (leaving the collar in place) and a guide rod is inserted into the drilled hole with the head guide still in position. A separate large diameter face drill is then employed to machine a flat counter-bore surface on the head of femur. This face drill has a bore to fit precisely over the guide rod and a flange feature which stops against the collar to limit the depth of the counter-bore to a planned position. This counter-bore later acts as a datum surface which a separate cylinder/chamfer cutter stops cutting against and it corresponds exactly with the internal planar surface of the resurfacing head implant, therefore it can be seen how the patient specific guide controls all aspects of head implant position according to the pre-operative plan. Once the guide rod is in position and the face drill cut is made, the patient specific guide is removed by first unlatching and removing the outer drill guide, then releasing the neck ring latch and then expanding it open to remove it from the femur. Preferably a separate cylinder/chamfer cutter is then employed to complete the machining of the head of femur which is also controlled by the by the guide rod and stops cutting when it reaches the counter-bore surface. Finally the guide rod is removed, a stem over-drill is used to enlarge the central hole to accept the head implant stem and the head of femur is then fully prepared ready for the head implant.

Generic Head Guide

This variant is a standard version of the head guide (not patient specific). There are several different sizes of main body, each size corresponding to a specific head implant size. When latched closed, the neck ring is cylindrical in shape and the internal diameter of the cylinder is slightly smaller than the diameter of the cylindrical head cutter for a given head size. The neck ring positions the central axis for the cylinder/chamfer cutter, therefore it will ensure that the cutter exit position coincides with the ring position (which is slightly smaller), and so it is impossible for the cutter to encroach/notch the femoral neck.

Preferably the collar is a single part, fitted onto the main body via a sliding fit and retained in position by a latch feature. Preferably a metal drill tube with a spiked end is inserted into the central hole of the collar and a drill (for example 5 mm in diameter) is then passed through the drill tube and a hole is drilled into the femur bone, corresponding to the central longitudinal axis of the resurfacing head implant. The collar is then removed and a guide rod is inserted into the drilled hole. The guide is removed by first unlatching and removing the collar, then releasing the neck ring latch and then expanding it open to remove it from the femur.

The neck ring being cylindrical is not always close fit on the neck (as the patient specific version is) therefore the surgeon must bias it into the appropriate position before drilling the hole in the femur. In one embodiment the neck ring has the addition of several internal flexible fingers to help centralise and stabilise it on the femoral neck. Alternatively or additionally the neck ring latch may have a multitude of engaging positions (in the form of a ratchet) so that the ring can be compressed down to fit the femoral neck and provide a more stable fit. In the first ratchet latch position (or single position if there is only one) the neck ring is circular and slightly smaller than the head cutter size (this ensures that the cutters used to prepare the head do not encroach/notch into the femoral neck) then as the ratchet is advanced, the ring becomes oval shaped but the axis for drilling remains central so it still guards against encroachment/notching. Preferably a flag extends from the neck ring which is positioned to be in line with the inferior femoral neck. This is a useful visual reference as the first few centimetres of the inferior femoral neck approximately indicated the desired head axis.

In another form, the main part of the guide incorporates jaws which clamp with an opposing grip around the femoral neck just beyond the head. Preferably the shape of the jaws is defined preoperatively to exactly fit to the specific patient's bone and orientate the guide according to a pre-operative plan. Alternatively, they could be shaped to fit a generic neck of femur of a certain size or size range. Preferably, there are two opposing jaws but there could be more than two and up to six, e.g. 2, 3, 4, 5 or 6. Due to this clamping action it is not necessary to hold the guide against the bone or to fix it with separate pins or screws as is often required with patient specific guides.

The guide has a resilient hinge allowing the jaw portion to expand and pass over the head of the femur to clamp on the neck. This expansion occurs because the portion to one side of the resilient hinge is manually compressed (for example between thumb and forefinger) and as this portion is compressed the jaw portion to the other side of the hinge expands. Preferably, there are two resilient hinge features but there could be more than two and up to six, e.g. 2, 3, 4, 5 or 6. A separate locking collar is inserted and tightened, preferably via a screw thread which blocks expansion and increases the clamping force on the neck. Alternatively, a bayonet fitting or a frictional fit could be used to attach the locking collar. Once assembled with the locking collar the guide is firm and stable on the femur bone and positioned according to the pre-operative plan. Preferably, a drill guide part is inserted into the locking collar via a bayonet fitting. Alternatively, a screw thread or friction fit could be used to attach the drill guide or the drill guide could be an integral part of the locking collar. A drill is then passed through the drill guide and a hole is drilled into the femur corresponding to the central longitudinal axis of the resurfacing head implant. Once the drill guide is removed, a guide rod is inserted into the hole with the assembled guide still in position. A separate planar face cutter is then employed to machine a flat surface on the head of femur. This planar face cutter has a bore to fit precisely over the guide rod and a flange feature which stops against the locking collar to limit the depth of the machined flat surface. This flat surface later acts as a datum surface that the other rotary cutters stop cutting against and it corresponds exactly with the internal planar surface of the resurfacing head implant, therefore it can be seen how the patient specific guide controls all aspects of head implant position according to the pre-operative plan. Once the guide rod is in position and the planar cut is made, the patient specific guide is removed by first removing the locking collar and then expanding it to pass over the head of femur. Preferably a combined cylinder and chamfer rotary cutter is then employed to complete the machining of the head of femur which is also controlled by the by the guide rod and stops cutting when it reaches the planar surface. Finally the guide rod is removed, a larger over-drill is used to enlarge the central hole to accept the head implant stem and the head of femur is then fully prepared for the head implant. In certain embodiments of this form of the guide, there can be provided at least one locking means in the region of the jaw portion. This locking mechanism can act to restrict or prevent opening of the distal jaw portion when said locking mechanism is activated. This can help to secure the jaw portion around the femur head when the guide is in use. Typically, the locking mechanism will be positioned to the side of the jaw portion so as not to compromise access to the cavity of the jaw portion from the distal end. In some forms, the locking means can comprise a latch. Such a latch may have a ratchet feature, where there are a number of positions to which the latch can be tightened. Other suitable mechanisms will be well known to the skilled person. In some arrangements there may be a locking mechanism on either side of the jaw portion, to effect even more securing over the femur neck when the guide is in use. It is preferred that there should be relatively easy access to the one or more locking mechanisms when the guide is in place, so that the user can activate the locking mechanism and also release it in order to be able to remove the guide once it has been appropriately used. Easier access may be provided via the use of longer tabs or the like on the locking mechanism(s) which can be used to activate and release the mechanisms from a distance if the actual locking mechanism itself is hard to access when in use due to the proximity of e.g. soft tissue or bone.

Examples of the invention will now be described by referencing to the accompanying drawings:

FIG. 1-15 shown the patent specific head guide.

FIG. 6 shows the guide main body in the expanded/open position being fitted to the femur bone.

FIG. 7 shows the main body assembled on the femur bone with the latch secured.

FIG. 8 is an exploded view showing all 4 parts being assembled together.

FIG. 9 shows a hole being drilled into the femur bone.

FIG. 10 shows the partially assembled guide, with collar insert removed with a guide rod inserted in the drilled hole.

FIG. 11 is a partially cross sectioned view showing the planar face drill advancing over the guide rod.

FIG. 12 is a partially cross sectioned view showing the planar face drill at full depth.

FIG. 13 is a partially cross sectioned view showing the completed face cut and with the guide rod still in position.

FIG. 14 shows a separate rotary cutter advancing over the guide rod.

FIG. 15 shows the separate rotary cutter at full depth.

FIG. 16 shows the final head implant in position on the femoral bone.

FIG. 17 is the main body in the expanded/open position.

FIG. 18 is an exploded view showing all three parts, main body, collar and drill tube.

FIG. 19 shows all three parts assembled together on the femur bone.

FIGS. 20-37 show an alternative embodiment head guide

FIG. 20 is the guide body in the relaxed state.

FIG. 21 is the guide body in the expanded state.

FIG. 22 is another view of the guide body in the relaxed state.

FIG. 23 is another view of the guide body in the expanded state.

FIG. 24 is the assembled guide.

FIG. 25 is an exploded view of FIG. 24.

FIG. 26 is another exploded view of the assembled guide.

FIG. 27 shows the guide main body on a femur bone.

FIG. 28 shows a cross section of the guide body as it is expanded over the femoral head.

FIG. 29 shows a cross section of the guide body assembled on a femur bone.

FIG. 30 shows the assembled guide on a femur bone.

FIG. 31 is an exploded view of FIG. 30.

FIG. 32 shows the assembled guide on a femur bone with a drill about to be inserted.

FIG. 33 shows the partly assembled guide on a femur bone with a guide rod placed in the drilled hole.

FIG. 34 is a cross sectioned view of FIG. 33

FIG. 35 is a cross sectioned view of the partly assembled guide on a femur bone with a planar face cutter about to slide onto the guide rod.

FIG. 36 is a cross sectioned view of the partly assembled guide on a femur bone with a planar face cutter having cut to its fullest extent.

FIG. 37 is a cross sectioned view of the femur bone with guide rod inserted showing the completed planar face cut.

The patent specific head guide will now be described with reference to FIGS. 1-5.

Figure 1:
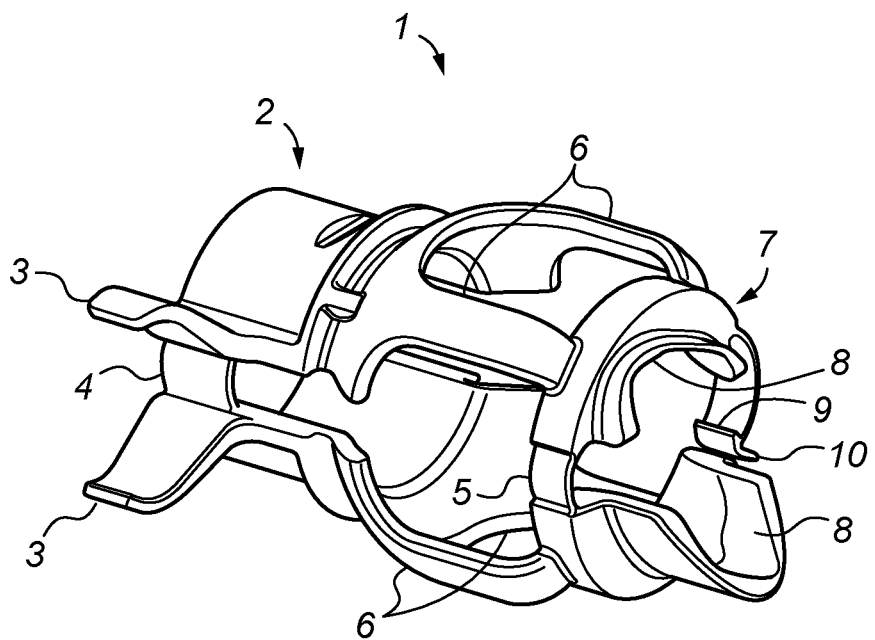
FIG. 1 shows head guide main body.
Figure 2:
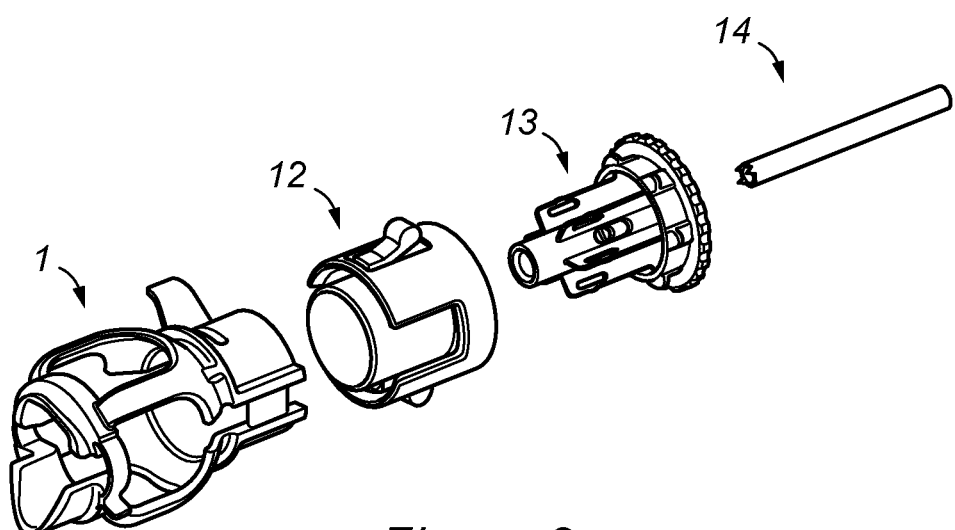
FIG. 2 is an exploded view showing all four parts, main body, collar, collar insert and drill tube.
Figure 3:
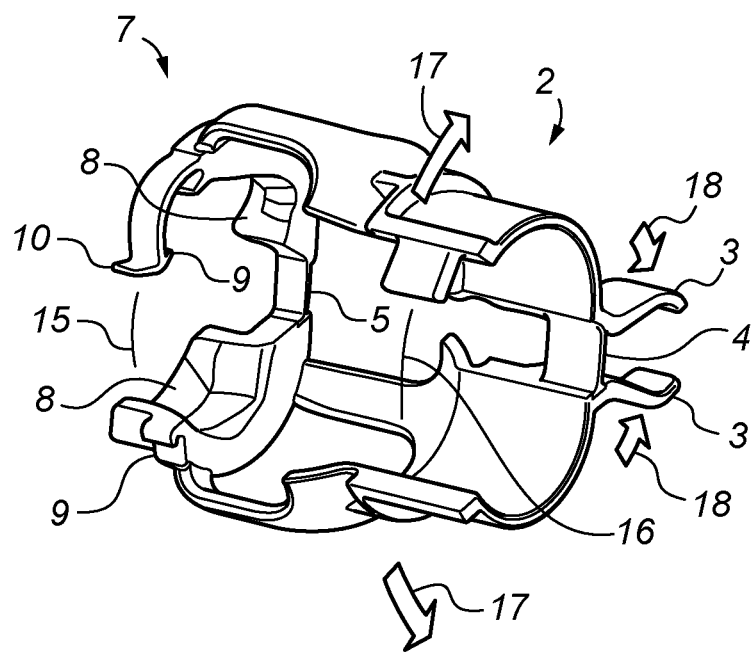
FIG. 3 is the main body in the expanded/open position.
Figure 4:
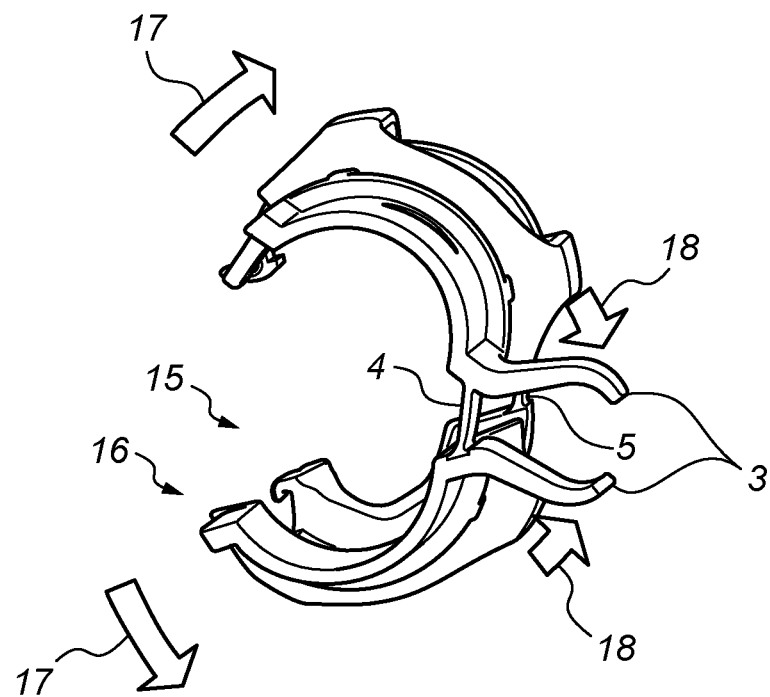
FIG. 4 is another view of the main body in the expanded/open position.
Figure 5:
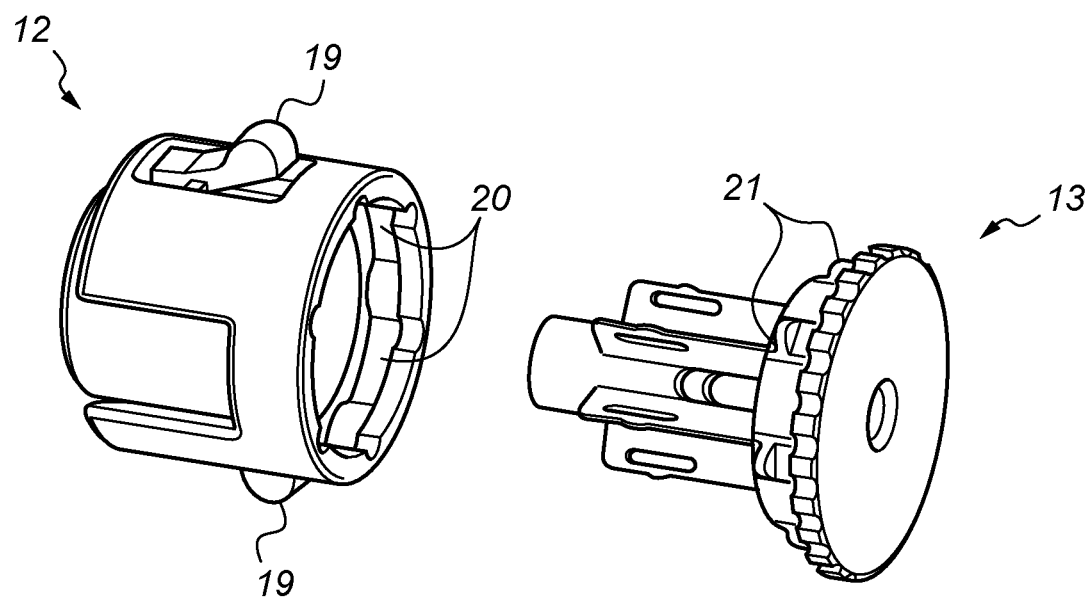
FIG. 5 shows the 2 part collar (collar and insert).
Figure 6:
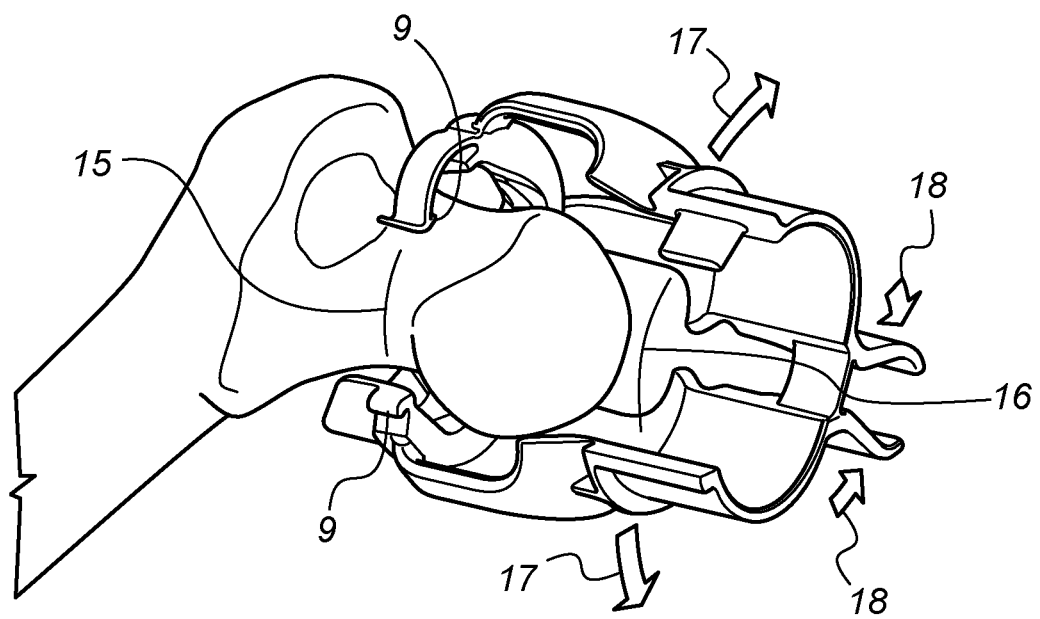
FIGS. 6-16 show the sequence of use of the patent specific head guide.

In FIG. 1 it can be seen that the main body [1] is manufactured as a single part consisting of two approximately cylindrical rings, one at each end with a multitude of connecting struts [6] (for example two, four or six struts). One ring is intended to be positioned around the femoral neck (neck ring [7]) and the other is positioned at the opposite side of the femoral head (head ring pp. The neck ring [7] has an integral hinge [5] on one side and an opening [15] at the other side. The head ring [2] has an integral hinge [4] on one side and an opening [16] on the other side. The two hinges are arranged to be axially aligned, so that they act together (similar to two hinges on a gate or door). The head ring has two paddle features [3] which extend outwards to the other side of the hinge [4]. When the paddles are pressed together in the direction of arrows [18] (for example between thumb and forefinger) the two halves of the main body, are hinged apart in the direction of arrows [17] (similar to a hair claw) as shown in FIGS. 3 and 4. This allows it to be assembled over the femoral head/neck bone, either from one end or from the side during the resurfacing operation (as shown in FIG. 6). The free position of the guide main body is closed (as in FIG. 1) so that it returns to this position as the grip on the paddles is relaxed.

The internal surfaces [8] of the neck ring are defined preoperatively to exactly fit to the specific patient's bone and hence to orientate the guide according to a preoperative plan. The neck ring has a latch [9] at the opening side (opposite the hinge) for fastening it closed. The latch can be opened manually with release tag [10] to remove it after use. As the neck ring extends almost fully round the femoral neck, it will only fit and close properly in the distinct position it is intended to fit.

Figure 8:
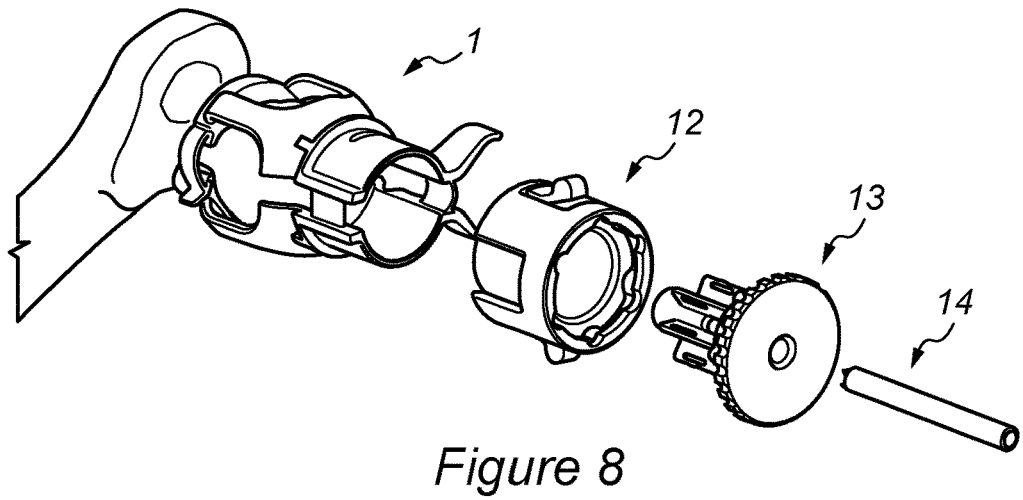

All parts of the head guide are shown in FIG. 8, main body [1], collar [12], collar insert [13] and drill tube [14]. The collar [12] has a sliding fit onto the main body [1] and is held in position by two latches [19]. Once fitted, the collar captivates the head ring in the closed position, therefore once the neck ring latch [9] is closed and the collar [12]

assembled, the guide is very firm and stable on the femur bone. The collar insert [13] fits into the collar via a bayonet fitting (the collar insert [13] has a male bayonet fitting [21] and the collar [12] has female bayonet fitting [20] which is shown clearly in FIG. 5.

The in-use function of the patent specific head guide will now be described with reference to FIGS. 6-16.

Figure 7:
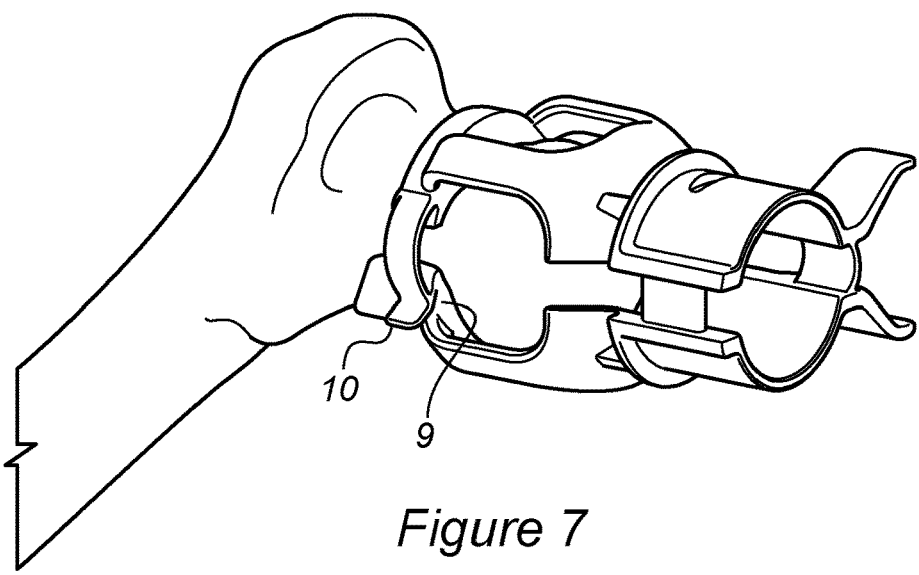
Figure 9:
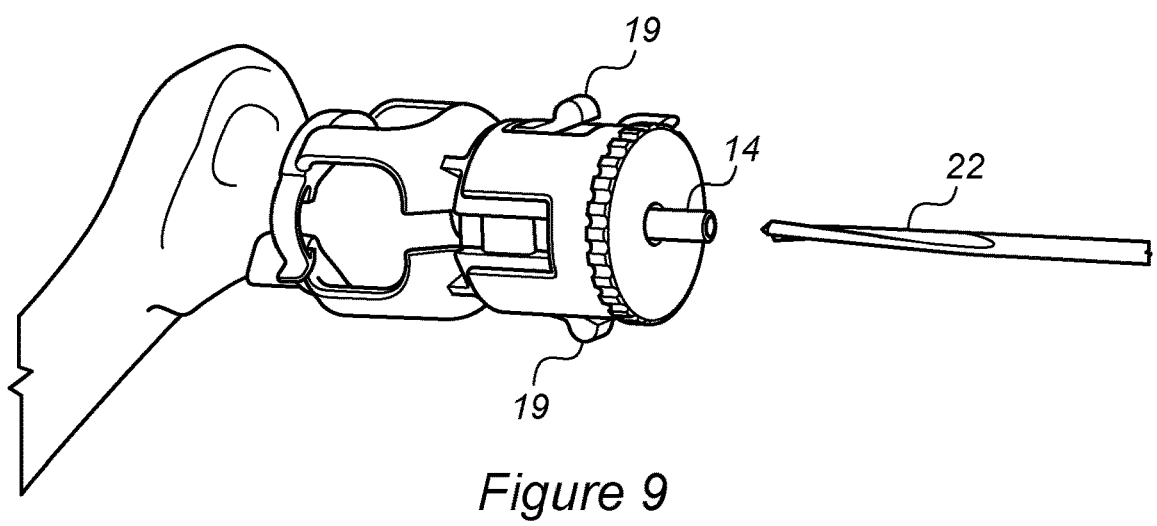
Figure 10:
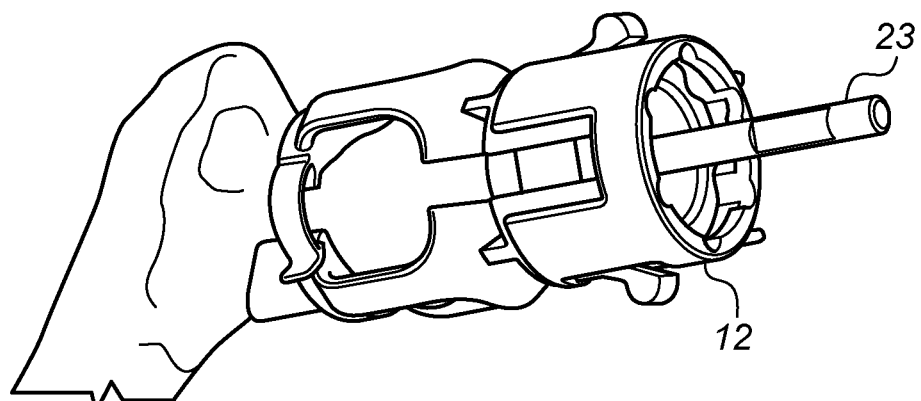
Figure 11:
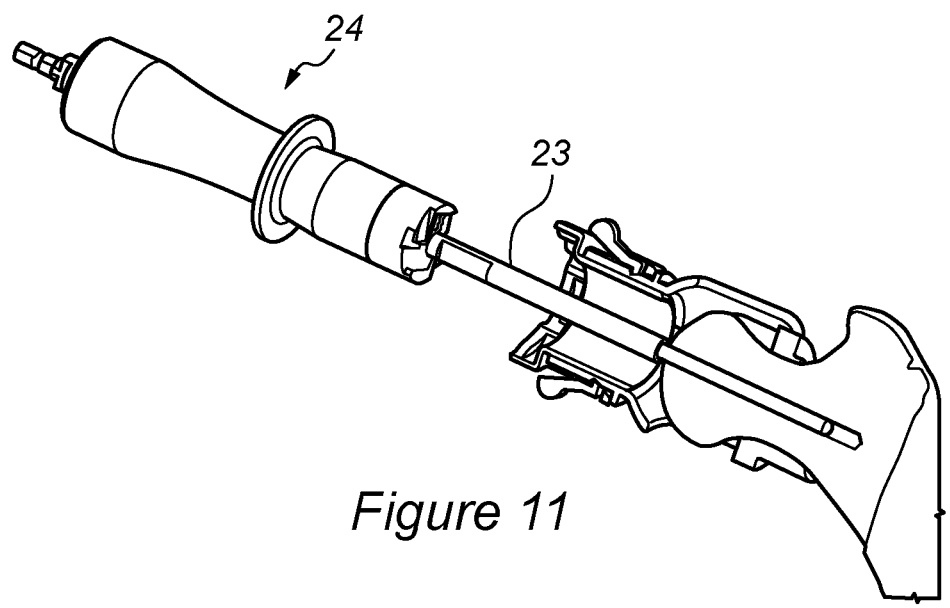
Figure 12:
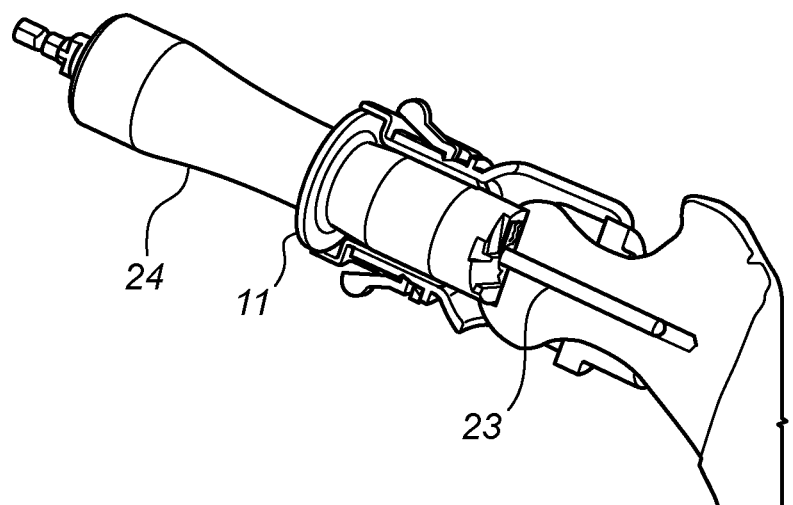
Figure 13:
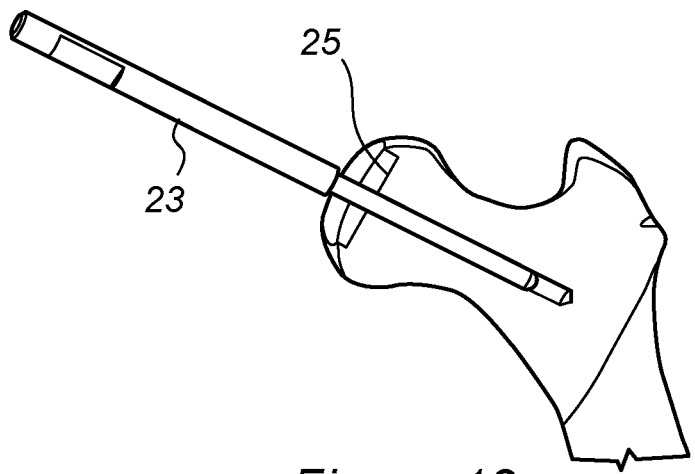
Figure 14:
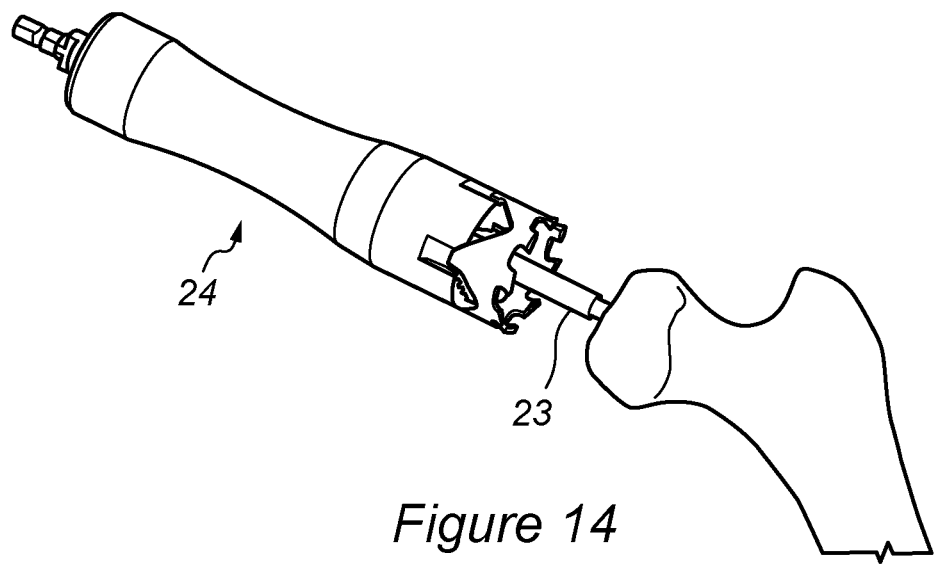
Figure 15:
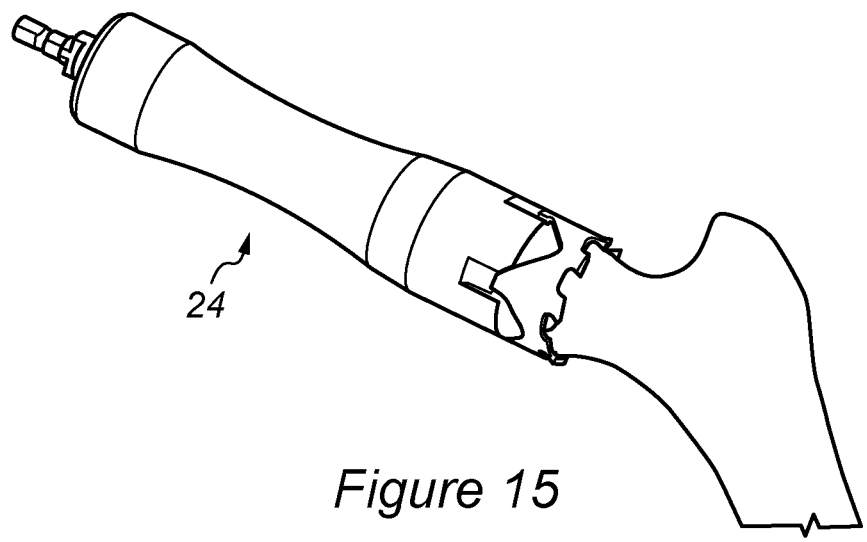
Figure 16:
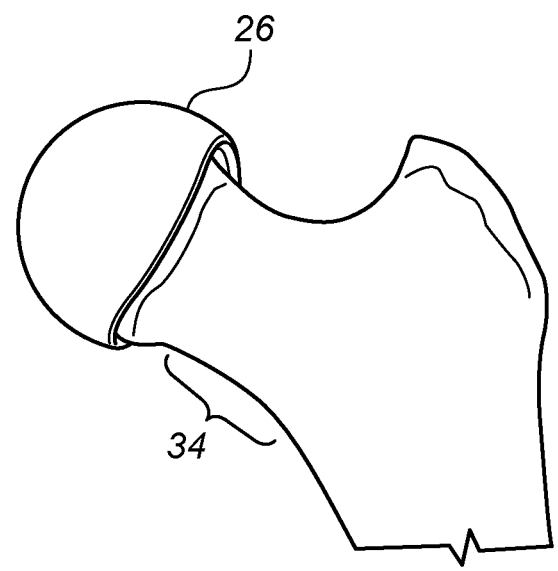

The paddles are pressed together (for example between thumb and forefinger) to assemble the main body over the femoral head/neck bone, either from one end or from the side as shown in FIG. 6. It is then allowed to close over the head/neck and manipulated to the position of the planned fit. The latch [9] will close once this distinct position is found as shown in FIG. 7. The other parts are then assembled onto the main body (collar [12], collar insert [13], and drill tube [14] as shown in FIG. 8. The spiked end of the drill tube is tapped into the femoral head and a drill [22] (for example 5 mm in diameter) is then passed through the drill tube to drill a hole into the femur bone corresponding to the central longitudinal axis of the resurfacing head implant as shown in FIG. 9. The drill tube and insert are removed (leaving the collar [12] in place) and a guide rod [23] is inserted into the drilled hole with the head guide still in position as shown in FIG. 10. A separate face drill [24] is then advanced (as shown in FIGS. 11 and 12) to machine a flat counter-bored surface on the head of femur. This face drill has a bore to fit precisely over the guide rod and a flange feature [11] which stops against the collar [12] to limit the depth of the counter-bore to a planned position. This counter-bore [25] later acts as a datum surface which a separate cylinder/chamfer cutter [24] stops cutting against and it corresponds exactly with the internal planar surface of the resurfacing head implant. Therefore it can be seen how the patient specific guide controls all aspects of head implant position according to the pre-operative plan. The patient specific guide is removed (leaving the guide rod [23] in position as shown in FIG. 13) by first unlatching and removing the collar [12], then releasing the neck ring latch [9] via tab [10] and then expanding it open to remove it from the femur. A cylinder/chamfer cutter [24] is then employed to complete the machining of the head of femur which is also controlled by the by the guide rod and stops cutting when it reaches the counter-bore surface [25] as shown in FIGS. 14 and 15. Finally the guide rod is removed, a stem over-drill (not shown) is used to enlarge the central hole to accept the head implant stem and the femur bone is then fully prepared ready for the head implant [26] (shown in final position in FIG. 16).

Figure 17:
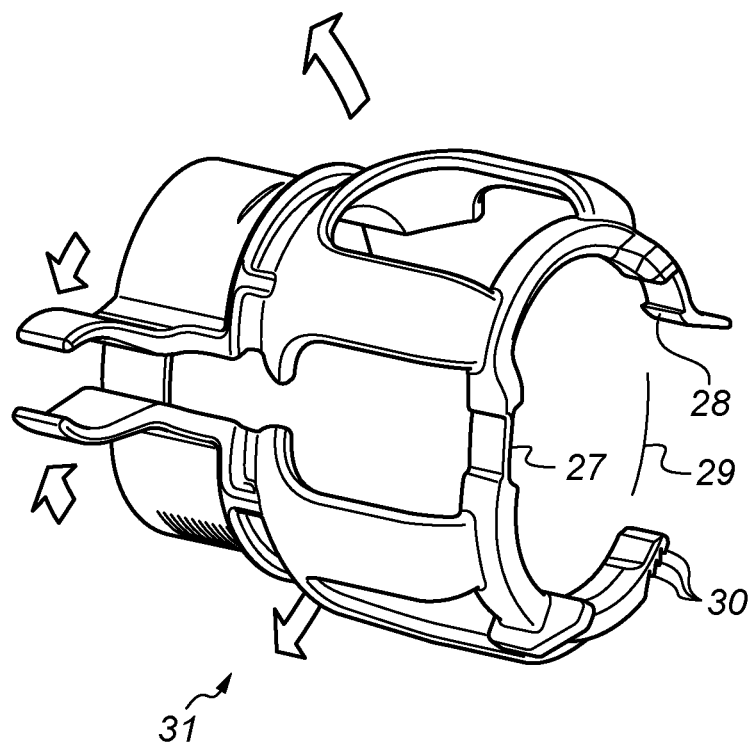
FIGS. 17-19 show an alternative embodiment generic (non-patient specific head guide)
Figure 18:
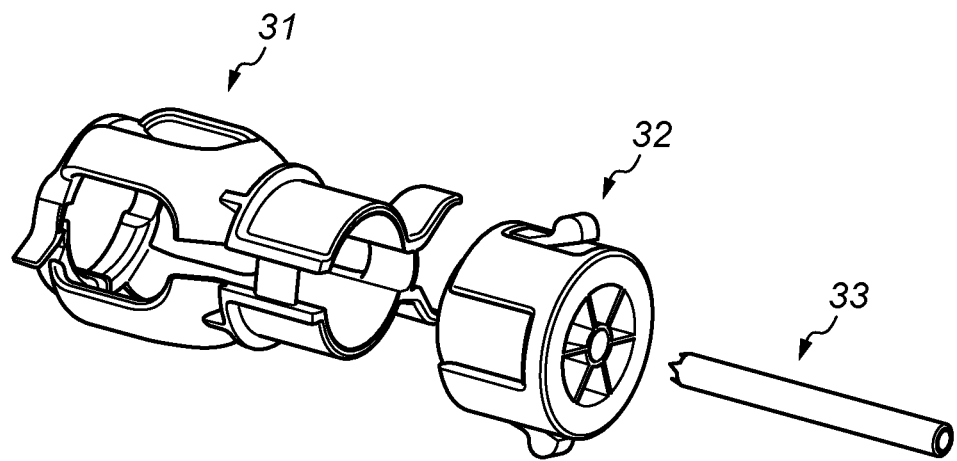
Figure 19:
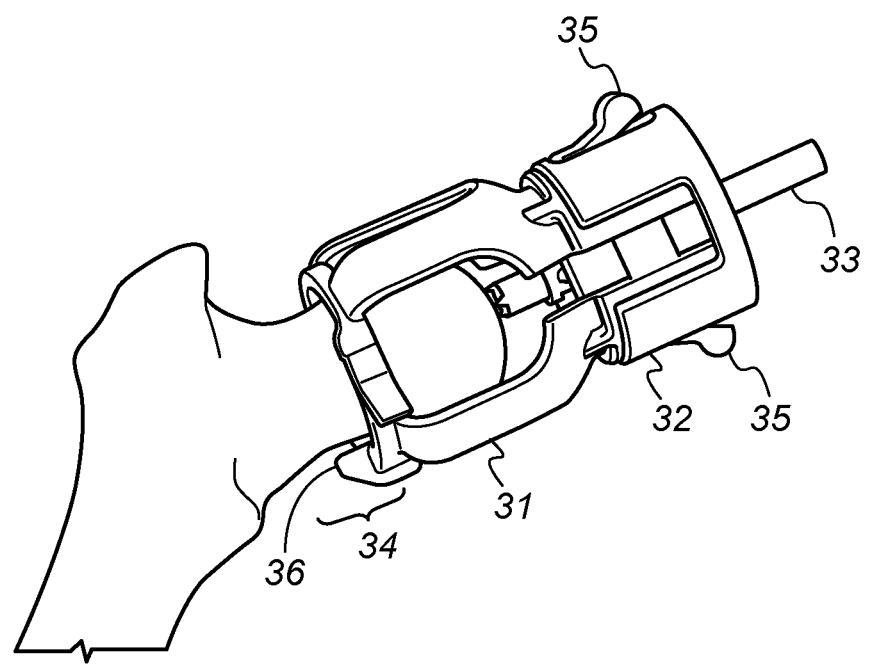

An alternative embodiment, the generic (non-patient specific) head guide will now be described with reference to FIGS. 17-19. It is very similar to the patent specific head guide, therefore only the features which are different will be described.

This embodiment is a standard version of the head guide (not patient specific). It can be seen in FIG. 17 that the neck ring consists of two half rings with an integral hinge [27] on one side and an opening [29] at the other side. In this embodiment the neck ring latch [28] has a multitude of engaging positions [30] in the form of a ratchet, however alternatively there is only one latch position (similar to the patient specific version). There are three parts to this guide, consisting of main body [31], insert [32] and drill tube [33] as shown in FIG. 18.

When latched closed, the neck ring is cylindrical in shape and the internal diameter of the cylinder is slightly smaller than the diameter of the cylindrical head cutter for the corresponding head size. The collar [32] is fitted onto the main body via a sliding fit and retained in position by two latch features [35]. A flag [36] extends from the neck ring which is positioned to be in line with the inferior femoral neck. This is a useful visual reference as the first few centimetres of the inferior femoral neck [34] approximately indicated the desired head axis. This can be seen in FIG. 19 where the fully assembled guide is mounted on the femur bone.

In this embodiment the head guide is used to position the guide rod (and therefore the central axis of the head implant) however it does not control the depth of the face drill counter-bore. This is controlled by another means, using the femoral head surface as a datum. The neck ring being cylindrical is not always close fit on the neck (as the patient specific version is) therefore the surgeon must bias it into the appropriate position before drilling the hole in the femur.

An alternative embodiment will now be described with reference to FIGS. 20-37

Figure 24:
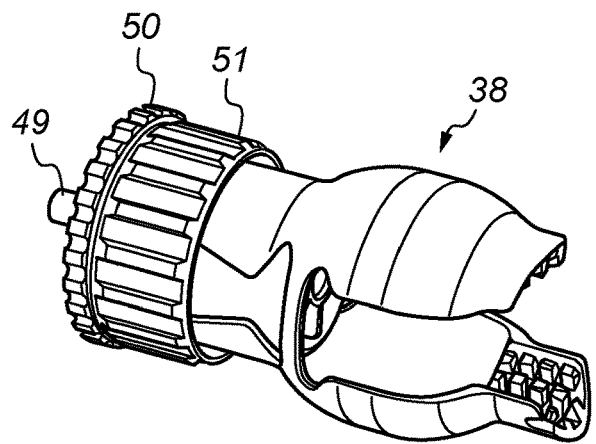
Figure 25:
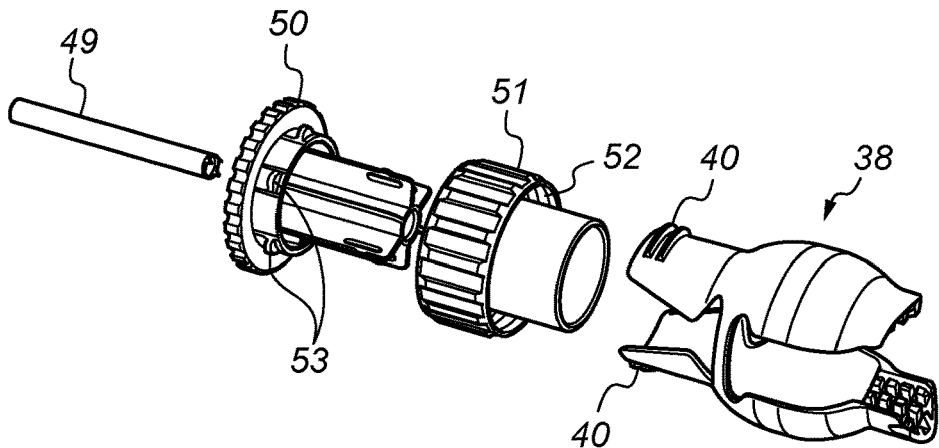
Figure 26:
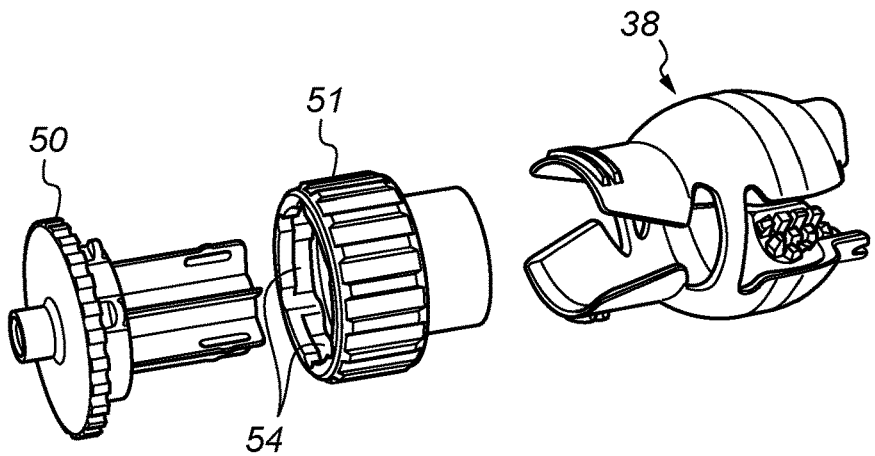

In FIG. 20-23 the anatomy of the guide body (38) will be described as having a largely cylindrical portion (39) with a bore (42) and partial screw thread (40) with two slot opening (41) ending in a two thinned resilient connections (45) described hereafter as the resilient hinge. To the other side of the resilient hinge is a largely spherical portion (44) with bore (46) with two opening slots (48) and internal jaws (47) defined to make mating contact with the femoral bone (55) shown in later figures. It can be seen in FIGS. 21 and 23, that as the largely cylindrical portion (39) is compressed, for example with a manual grip between thumb and forefinger (not shown), the resilient hinges (45) flex and expansion of the largely spherical portion (44) occurs. The partial screw thread (40) also acts as a finger grip to prevent the fingers slipping off the guide body. As the manual grip is relaxed, the guide body returns to the relaxed state as shown in FIGS. 20 and 22. In FIGS. 24-26 all parts of the assembled guide are identified as guide body (38), locking collar (51), drill guide (50) and spiked tube (49). As shown in these figures, locking collar (51) fits precisely with the largely cylindrical portion of the guide body both on the internal bore (42) and external cylinder with screw thread (40 & 52). Therefore when locking collar (51) is assembled and tightened via the screw thread, both compression and expansion of largely cylindrical (39) and spherical (44) portions are prevented.

Figure 27:
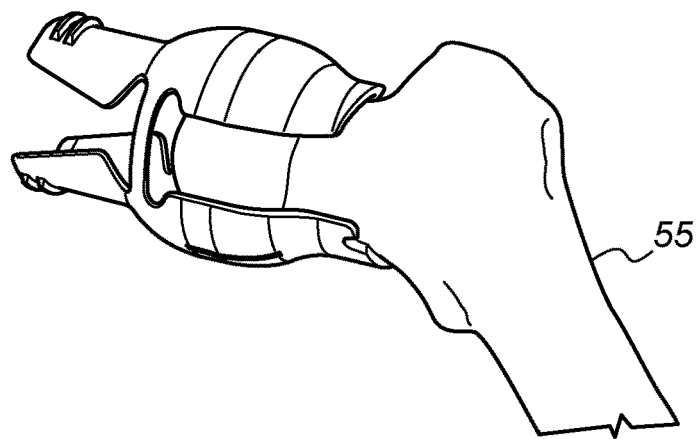
Figure 28:
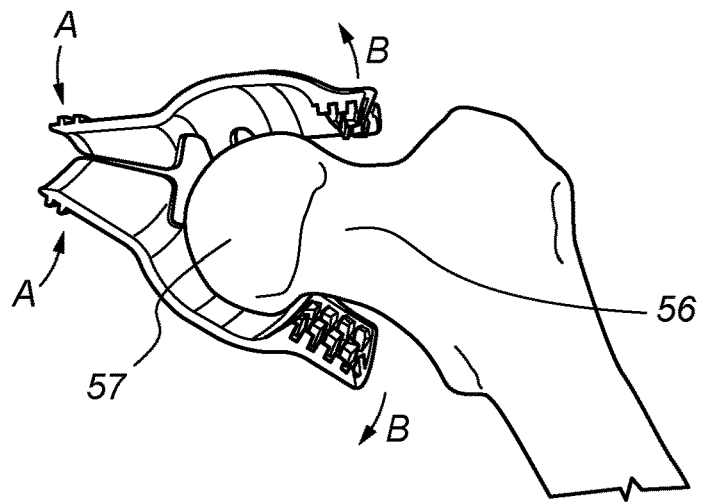
Figure 29:
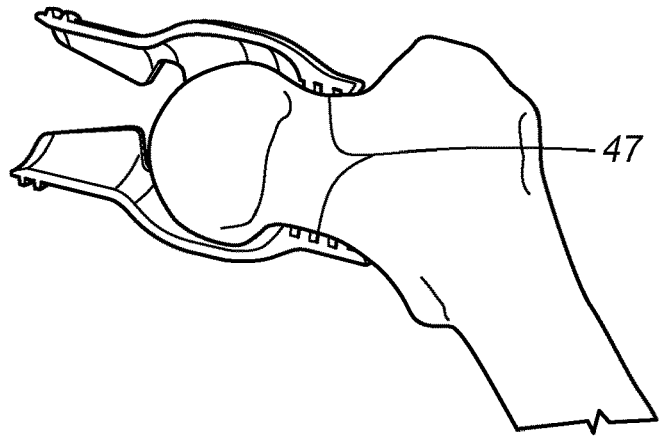
Figure 30:
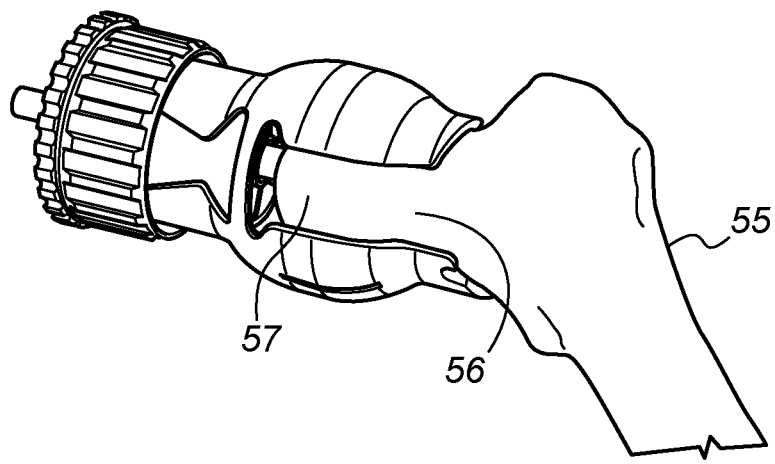
Figure 31:
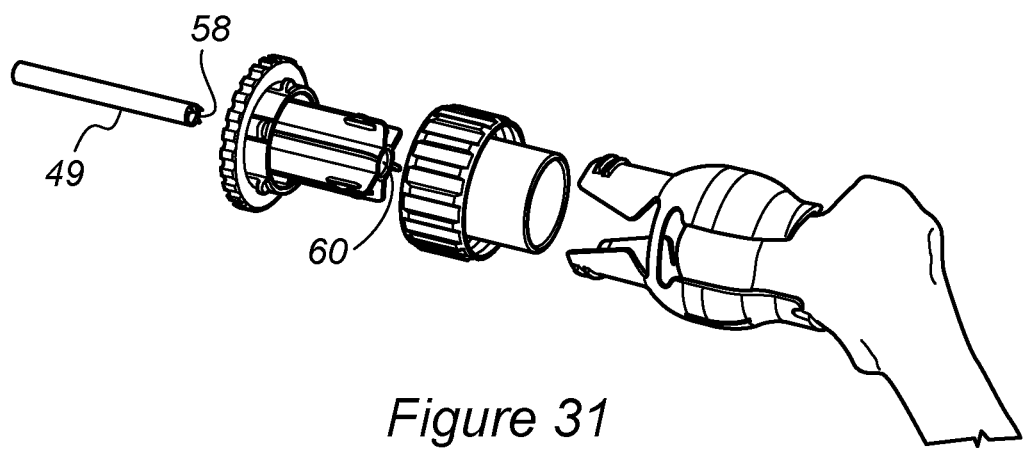
Figure 32:
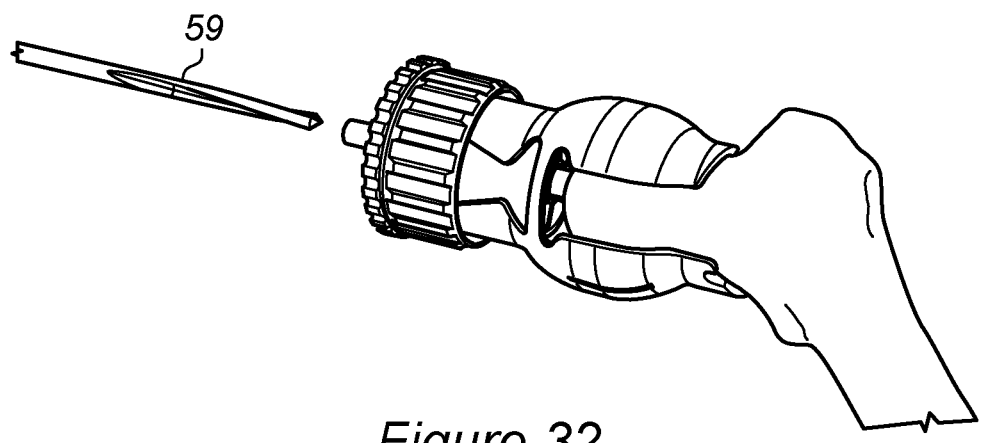
Figure 33:
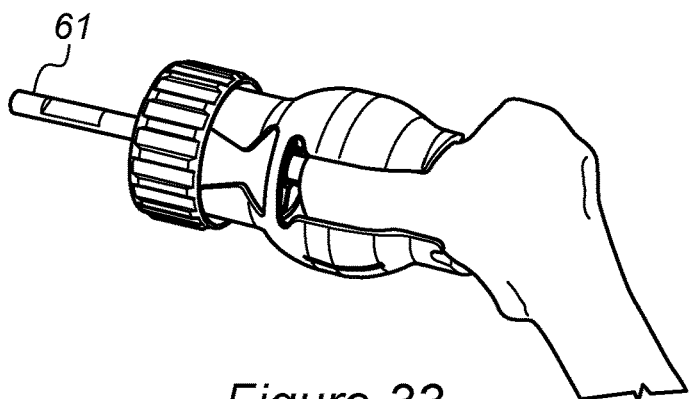
Figure 34:
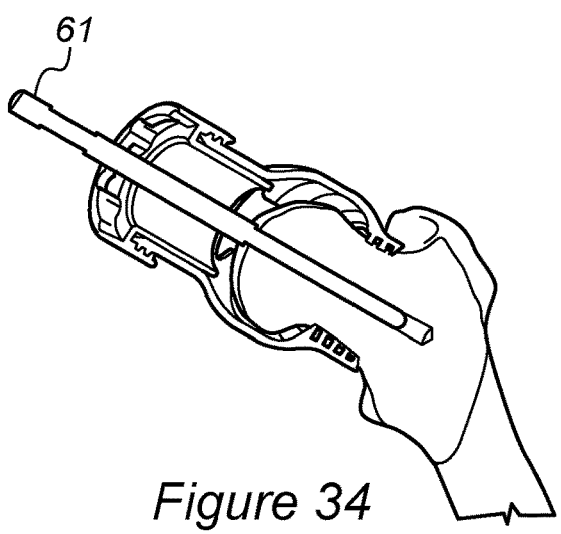
Figure 35:
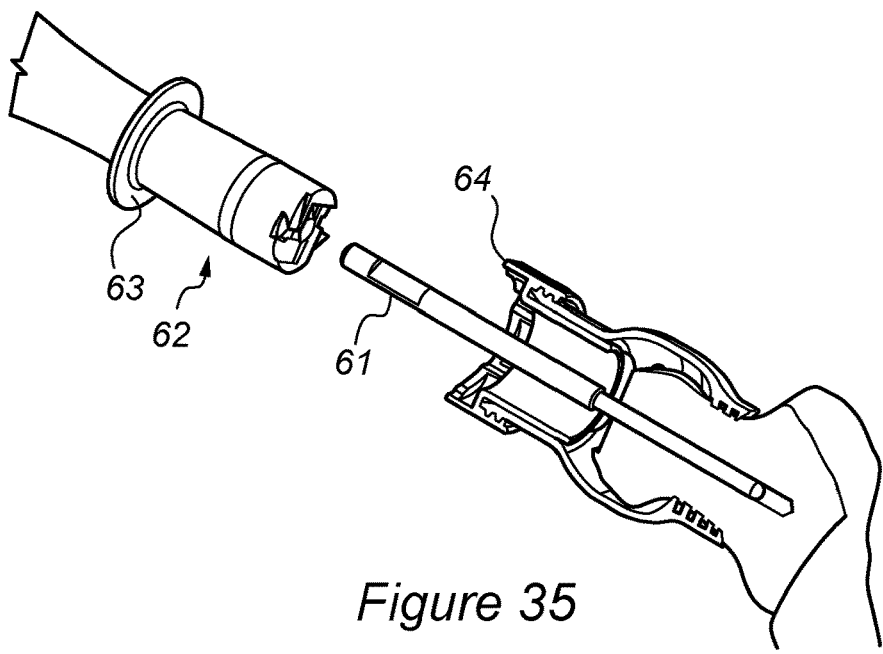
Figure 36:
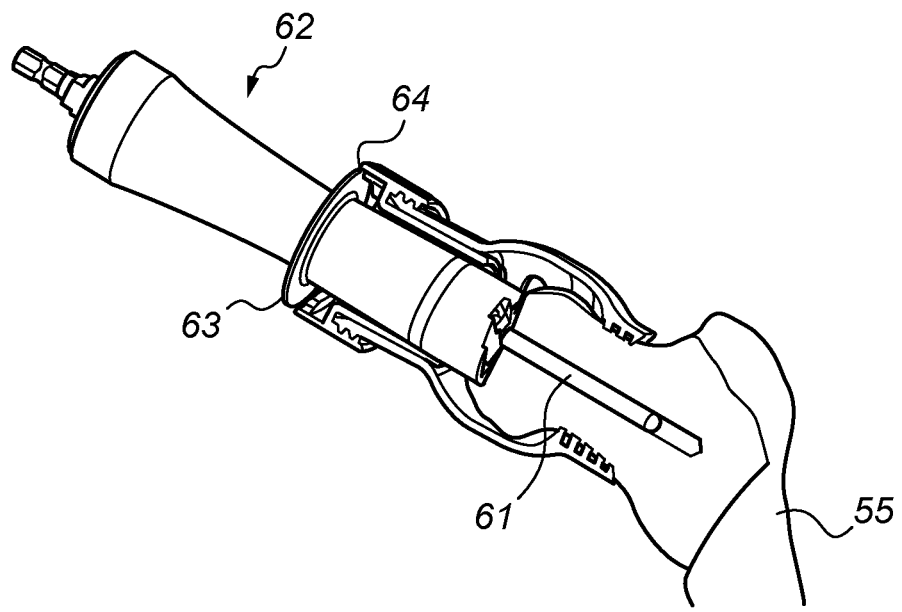
Figure 37:
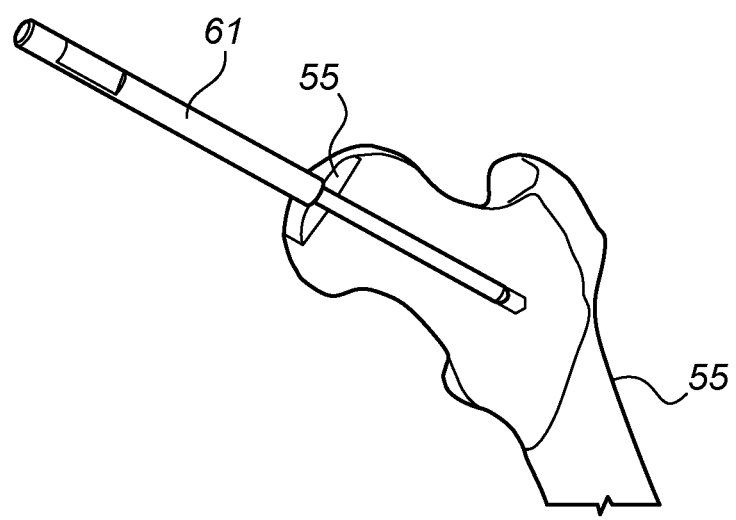

In use during a hip resurfacing operation, the guide body must first be assembled over the femoral head (57) as shown in FIGS. 27-29 using the method described above. FIGS. 27 and 29 show the mating fit of the jaw teeth (47) with the femoral neck (56). Preferably the profile of the jaw teeth is defined from a preoperative plan but alternatively could be shaped to fit a generic neck of femur of a certain size or size range. It can be seen how the two opposing jaws mating with the femoral neck control the three dimensional position of the guide relative to the femur bone preferably according to the preoperative plan. When the locking collar is assembled, the guide body becomes rigid and further acts to maintain its position. Furthermore as the locking collar is assembled with the guide body the grip force is increased as now described. A pretension allowance is built into the guide body so that as the locking collar is inserted, it slightly expands the cylindrical bore which compresses the largely spherical portion (38) to the other side of the resilient hinge (45) and tightens the grip on the femoral neck (56). Clearly shown in FIG. 31 is the spiked tube part (49) which fits into the bore (60) of the drill guide. The sharp spikes (58) on the spiked tube penetrate the femoral head slightly and prevents the drill (59) from skating off line as it enters the femoral head. The drill (59) shown in FIG. 32 makes a reference hole in the femur (55) which exactly coincides with the longitudinal axis of the resurfacing head component preferably as defined by the preoperative plan. In FIGS. 33-36 it can be seen that the drill guide (50) has been removed and a guide rod (61) is placed in the drilled hole which also coincides with the longitudinal axis of the resurfacing head component. A rotary cutter (62) then slides over the guide rod (61) and is rotated with a surgical power drill (not shown) to make a planar face cut on the femoral head. The depth of this face cut is controlled by a flange feature (63) on the rotary cutter (62) which makes contact with the end face (64) of the locking collar (51) acting as a stop feature as shown in FIG. 36. This planar cut surface (65) on the femoral head serves as a datum surface that the other rotary cutters stop cutting against and it corresponds exactly with the internal planar surface of the resurfacing head implant. Once the planar face cut is made, the guide is removed by first unscrewing the locking collar and then expanding the guide body over the femoral head, leaving the guide rod in position as shown in FIG. 37.

The invention claimed is:

1. A guide system for an implantable device, said guide system comprising
   a first component arranged to act as a clamp; and
   a second component arranged to engage an outer surface of and interact with the first component to restrict or prevent movement of said first component when clamped;
   wherein the first component comprises at least one actuating portion and at least one jaw portion;
   wherein the at least one actuating portion and at least one jaw portion each comprises opposing arms arranged either side of a hinge region; and
   wherein the actuating portion and jaw portion are arranged on either side of the hinge region such that when the actuating portion is compressed the jaw portion expands, and when the actuating portion is relaxed the jaw portion closes.

2. The guide system of claim 1, wherein said first component comprises a proximal region, said proximal region comprising an actuating portion and proximal jaw portion formed by the walls of said first component, said proximal region further comprising a cavity defined by the walls of said first component between the actuating portion and proximal jaw portion and wherein the cavity permits access to a distal region of the first component.

3. The guide system of claim 1, wherein the hinge region lies substantially perpendicular to the longitudinal axis of the first component.

4. The guide system of claim 1, where the hinge region is formed from the same material as the first component and is integral with the first component, the first component and the hinge region being a single piece.

5. The guide system of claim 1, wherein the at least one actuating portion comprises at least two opposing arms.

6. The guide system of claim 1, wherein the first component comprises a distal jaw portion being positioned at a distal region of the first component, wherein said distal region further comprises a locking mechanism to restrict or prevent opening of the distal jaw portion when said locking mechanism is activated, wherein said locking mechanism comprises a latch.

7. The guide system of claim 6, wherein said latch is releasable and is configured either:
   (i) to have one locking position; or
   (ii) to have a plurality of locking positions which allow a stepped progression of tightening the distal jaw portion.

8. A guide system for an implantable device, said guide system comprising a first component arranged to act as a clamp, said first component comprising at least one actuating portion and at least one jaw portion, said actuating and jaw portions arranged either side of at least one hinge region, said actuating portion being positioned at a proximal region of the first component and said jaw portion being positioned at a distal region of the first component, wherein said distal region further comprises a locking mechanism formed as a latch on the jaw portion to restrict or prevent opening of the distal jaw portion when said locking mechanism is activated.

9. The guide system according to claim 8, wherein the distal jaw portion comprises arms that are defined preoperatively to fit to a specific patient's bone and thereby orientate the guide system according to a preoperative plan.

10. The guide system according to claim 8, wherein the distal jaw portion comprises arms that are defined to fit approximately to certain size ranges of femoral necks without patient specific adaptations.

11. The guide system of claim 10, wherein the arms of the distal jaw portion are substantially the same length.

12. The guide system of claim 10, wherein the arms of the distal jaw portion are not the same length.

13. The guide system of claim 8, wherein the distal jaw portion comprises at least one gripping portion, wherein the gripping portion is profiled to increase frictional force with the intended item to be gripped.

14. The guide system of claim 13, where the gripping portion comprises a plurality of flexible fingers.

15. The guide system of claim 8, wherein the first component further comprises a portion between the proximal region and the distal jaw portion which has a ballooned profile, wherein the profile is approximately spherical.

16. The guide system of claim 8, further comprising a second component, wherein the second component is a locking collar which is configured to be placed over the proximal region of the first component to prevent the proximal jaw portion from opening.

17. A guide system for an implantable device, said guide system comprising a first component arranged to act as a clamp, said first component comprising at least one actuating portion and at least one jaw portion, said actuating and jaw portions arranged either side of at least one living hinge, said actuating portion being positioned at a proximal region of the first component and said jaw portion being positioned at a distal region of the first component, wherein said distal region further comprises a locking mechanism formed as a latch on the jaw portion to restrict or prevent opening of the distal jaw portion when said locking mechanism is activated.

* * * * *